(12) United States Patent
Mireles

(10) Patent No.: US 9,050,620 B2
(45) Date of Patent: Jun. 9, 2015

(54) DISPENSING AND HOUSING APPARATUSES FOR HAND SANITIZER AND OTHER DISPENSABLE PRODUCTS

(71) Applicant: Nicholas Stone Mireles, New York, NY (US)

(72) Inventor: Nicholas Stone Mireles, New York, NY (US)

(*) Notice: Subject to any disclaimer, the term of this patent is extended or adjusted under 35 U.S.C. 154(b) by 0 days.

(21) Appl. No.: 14/049,401

(22) Filed: Oct. 9, 2013

(65) Prior Publication Data

US 2015/0097005 A1     Apr. 9, 2015

(51) Int. Cl.
*B67D 1/07*     (2006.01)
*B05C 21/00*   (2006.01)
*A61L 2/16*     (2006.01)
*A61M 11/00*   (2006.01)

(52) U.S. Cl.
CPC . *B05C 21/00* (2013.01); *A61L 2/16* (2013.01); *A61M 11/00* (2013.01)

(58) Field of Classification Search
CPC .............. A61L 2/16; A61L 2/18; A61L 2/20; A61L 2/26; A61L 2202/10; A61L 2202/16; A61L 2202/20; A61L 2202/23; B05C 21/00; B05C 5/00; B05B 11/00; B05B 11/3098; B05B 11/0005; B05B 11/30; B05B 11/3042; A61M 11/00; A61M 11/006
USPC ........................................ 222/173, 175, 192
See application file for complete search history.

(56) References Cited

U.S. PATENT DOCUMENTS

| 5,187,468 | A | | 2/1993 | Garthwaite et al. | |
|---|---|---|---|---|---|
| 5,413,294 | A | | 5/1995 | Greenquist | |
| 5,978,495 | A | * | 11/1999 | Thomopoulos et al. | 382/124 |
| 6,415,960 | B1 | | 7/2002 | Fink | |
| 6,729,502 | B2 | * | 5/2004 | Lewis et al. | 222/181.3 |
| 7,178,696 | B2 | | 2/2007 | Christensen | |
| 2002/0066756 | A1 | * | 6/2002 | Kinsman | 222/547 |
| 2004/0253153 | A1 | * | 12/2004 | Barone | 422/123 |
| 2007/0164050 | A1 | | 7/2007 | Knight | |
| 2009/0236254 | A1 | * | 9/2009 | Jenkins et al. | 206/459.5 |
| 2010/0150785 | A1 | * | 6/2010 | Woolman et al. | 422/116 |
| 2010/0264168 | A1 | * | 10/2010 | Larabee | 222/162 |
| 2010/0294806 | A1 | * | 11/2010 | McDowell | 222/173 |
| 2011/0011886 | A1 | * | 1/2011 | Zaima et al. | 222/1 |
| 2011/0182652 | A1 | * | 7/2011 | Chung et al. | 401/218 |
| 2012/0037664 | A1 | * | 2/2012 | Dagel | 222/192 |
| 2012/0138637 | A1 | * | 6/2012 | Ciavarella et al. | 222/175 |
| 2012/0187146 | A1 | * | 7/2012 | Chopra | 222/52 |
| 2012/0273524 | A1 | | 11/2012 | Leifer | |
| 2013/0156482 | A1 | * | 6/2013 | Kaliebe et al. | 400/472 |
| 2013/0168408 | A1 | * | 7/2013 | Kubicz et al. | 222/1 |
| 2013/0200279 | A1 | * | 8/2013 | Chuang | 250/492.1 |
| 2014/0084028 | A1 | * | 3/2014 | Gunn | 222/175 |
| 2014/0204513 | A1 | * | 7/2014 | Del Padre et al. | 361/679.01 |
| 2014/0231451 | A1 | * | 8/2014 | Hammond et al. | 222/105 |
| 2014/0266575 | A1 | * | 9/2014 | Pelfrey | 340/5.2 |
| 2014/0334975 | A1 | * | 11/2014 | Geesbreght et al. | 422/28 |

OTHER PUBLICATIONS

Cynthia Kincaid, Hand Sanitizer Beneficial Inside the Restroom, CleanLink, Oct. 28, 2011, http://www.cleanlink.com/sm/article/Hand-Sanitizer-Beneficial-Inside-The-Restroom--13653.

\* cited by examiner

*Primary Examiner* — Patrick M Buechner

(57) ABSTRACT

A device for housing and dispensing hand sanitizers and other dispensable products in proximity to computers and other user technology. One embodiment of the device is a dispenser for hand sanitizer or other dispensable products that can be attached to a standard computer keyboard. In one embodiment, the device is a housing structure of similar size, appearance and feel as the standard "Enter" key.

8 Claims, 4 Drawing Sheets

DISPENSING AND HOUSING APPARATUSES FOR HAND SANITIZER AND OTHER DISPENSABLE PRODUCTS

BACKGROUND OF THE INVENTION

In our age of rapidly advancing technological change, businesses' and organizations' definitions of shared assets increasingly include public or shared computational and other technology resources. Many offices and educational institutions, as well as libraries, shopping malls and many other public spaces, provide public or shared computer workstations and other technology equipment and resources. These resources can be essential to modern communication and integral to commerce, but they can also pose a public health risk by spreading disease and contagions. This problem is acutely prevalent with shared computers, given the high degree of contact users must make with keyboards, touch-screens and other periphery equipment, but it more broadly affects a wide range of technology resources. The present invention offers a novel solution that, among other benefits, can help protect users of these resources and prevent the spread of disease.

A modern college campus provides just one example of the severity of the risk of contagion posed by common technology resources. From the hundreds of public computers in the libraries, to computers in each of several hundred classrooms, and various technology, science and media labs, shared technology resources are abundant on college campuses and essential for students and faculty. However, students and faculty often suffer from the experience of using a computer with greasy keys and other touch surfaces and otherwise interacting with technology resources that are generally unclean. Each time a person uses these resources, she must risk her health and wellbeing by being exposed to bacteria and viruses. The problem is perhaps most severe for low-income students who cannot afford personal computers or laptops and therefore must make greater use of shared resources. However, even students and faculty who own personal computing devices often must use shared technology resources for printing, specialized coursework and other activities. Unsanitary environments such as shared computing facilities risk the spread of disease and endanger the collegiate body as a whole.

Coincident with the modem rise of public computing resources, public health consciousness is higher than ever, particularly in the corporate and collegiate worlds. In many areas, initiatives to promote public health and more sanitary conditions are increasingly visible. In particular, hand sanitizers have become a common fixture in bathrooms, dining halls, gyms and most other public gathering places. Personal hand sanitizers have also been widely embraced, even to the extent that they are often distributed for free by corporations as hand-outs in marketing and recruitment campaigns. Indeed, recent global outbreaks of viruses and other contagions such as SARS, avian flu and the H1N1 virus have served to augment the already expanding sector of personal hygiene products. Industry estimates project sustained market growth for hand sanitizers and other personal hygiene products over the next few years, driven in part by modem public awareness and concern over the spread of disease and the need for readily accessible protection.

Nonetheless, modern health consciousness is often at odds with the requirements of shared technology resources. To date, the aforementioned efforts to promote public hygiene and prevent the spread of disease have failed to address the particular problems associated with shared technology resources and the needs of their users. For example, current hand sanitizer dispenser technology is inadequate to protect many shared technology users. Permanent wall fixture hand sanitizer dispensers like those commonly seen in public restrooms, if they happen to be installed in common technology areas, are generally useful only upon entering or leaving these areas, but they are generally not readily accessible to users while they are at individual workstations. Existing technology fails to provide dispensing where users need it most: at each individual keyboard or touch surface that poses a risk of contagion. Conversely, personal hand. sanitizers are insufficient because only those users who carry them, and apply them each time they use a particular computer or other technology resource, will be protected. Other users risk both contracting and transmitting disease if they have not had access to hand sanitizers and other health-related dispensables.

Indeed, even personal or portable technology such as smartphones and tablet computers can carry and spread disease, as keyboards and other touch surfaces are becoming ubiquitous in our daily lives but, unlike other things we use as frequently, cannot be washed or easily decontaminated. Accordingly, every technology user has a need for readily accessible hand sanitizer and other hygiene products that can protect them from contagion.

Given that each keyboard, touch surface and technology device is a potential site for germs to accumulate and spread, each user is put at risk when hand sanitizers and other personal hygiene products and dispensables are not readily accessible in proximity to each device or component. There is currently a critical unmet need in the marketplace, and technology users of all kinds, from students to corporate professionals to any other owner or user of modern technology devices, are put at risk due to the lack of dispensing technology adequately suited to this problem.

Wall-mounted sanitizer dispensers are common, and certain inventions have provided variations on the standard bathroom variety. For example, U.S. 2012/0273524 A1 discloses a wall mounted pump dispenser, designed to enable users to treat a surface such as a toilet seat with disinfectant formula stored in the device. Additionally, the need for personal sanitation on an immediate and frequent basis is demonstrated by the variety of different portable sanitation inventions. U.S. Pat. No. 7,178,696 enables an individual to both carry a spray bottle of personal hand sanitizer and selectively clip this article to clothing and the like. U.S. 2007/0164050 A1 employs the use of a lever-operated dispenser that can be clipped to a user's belt, waistline, baggage or similar devices. U.S. Pat. No. 6,415,960 provides a spray dispenser that is mounted to the user's arm. Yet, none of these devices are capable of protecting all users of technology resources in proximity to such devices; for example, the wall mounted varieties only protect certain users when they enter or leave public technology areas, and the personal dispenser varieties only protect users who purchase and regularly use them. Although these inventions acknowledge the widespread need for portable hand sanitizer and other hygiene products, none have sought to selectively attach dispensing devices to the keyboard or other parts of modern technology devices.

While no prior invention provides the user of a computational resource with hand sanitizer as provided herein, the use of the keyboard for attaching a technology periphery device has been documented, U.S. Pat. Nos. 5,187,468 and 5,413,294 both provide users with a manner of fastening technology peripheries. However, no mechanism is disclosed for attaching a dispenser device, particularly one suited to hand sanitizer or other personal hygiene products, to address the needs of modern technology users.

Substantial scientific evidence has proven the benefits of hand sanitation, and recent research further emphasizes the strong correlation between the availability of personal disinfectants in high traffic areas and use to protect individuals. Brian Sasoni, Vice President of Communications for the American Cleaning Institute in Washington, D.C., claims recent studies show that "if you make it easy for people, if you put hand sanitizer in front of them to use, the more likely they are to use it." Nonetheless, the need for dispensing technology in close proximity to keyboards and other technological devices remains critically unaddressed.

The present invention solves this pressing need for protecting public health and wellbeing in connection with technology facilities and equipment. It provides a novel apparatus that overcomes the inadequacies of current dispensing technology, allowing dispensable hygiene products to be readily accessible at each keyboard, touch surface and other technology device, periphery, component or accessory (collectively, "User Technology"). The invention enables corporations, universities and other providers of public or shared technology resources to protect their users from the spread of many diseases. Moreover, it could allow any owner or user of modern technology to protect herself by providing ready access to hand sanitizer, health-related and other dispensable products (collectively, "Dispensables"). Moreover, even beyond the realm of User Technology, the present invention can provide ready access to Dispensables to users of non-technology devices and equipment.

BRIEF SUMMARY OF THE INVENTION

A device for housing and dispensing Dispensables in proximity to User Technology and other objects. The device comprises a dispenser for hand sanitizer or other Dispensables that can be attached to a standard desktop keyboard, other User Technology or other objects. In one embodiment, the device could comprise a housing structure or means that could be attached to an object. Preferably, said housing could have a similar size, appearance and feel as the standard "Enter" key.

For a better understanding of the invention, reference is made to the following detailed description of the preferred embodiments of the invention, taken in conjunction with the accompanying drawings.

DESCRIPTION OF THE PREFERRED EMBODIMENT

Figure 1:
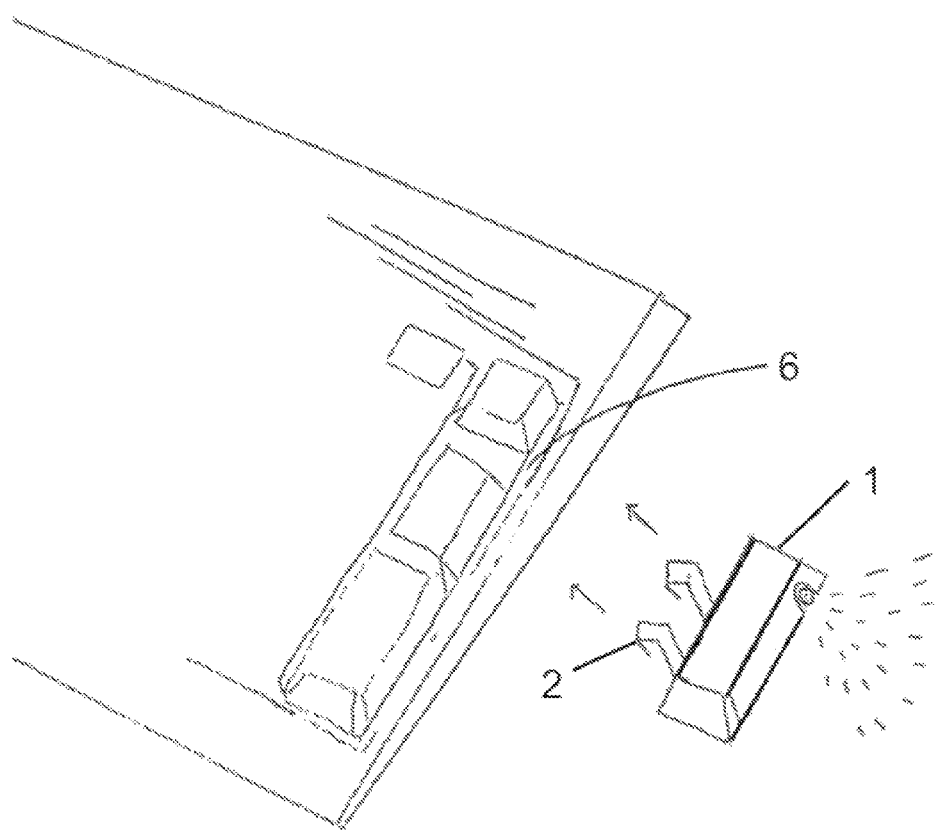
FIG. 1 is a perspective view of a keyboard hand sanitizer attachment that supports and suspends a small bottle of hand sanitizer from a keyboard or other electronic input device according to a first preferred embodiment of the invention.

One embodiment of the invention is a hand sanitizer dispenser that can be attached to the side of a standard desktop keyboard (depicted in FIG. 1). The housing of such embodiment has the same size, appearance and feel as the standard "Enter" key, but it contains a small perfume size bottle of hand sanitizer, which may be replaceable, disposable or refillable. The bottle is held underneath such key housing by a metal fastening unit with two clip features (depicted in FIG. 2). Two arms are inserted into the face of the keyboard and suspend such housing above the surface on which the keyboard rests. The arms are an extension of the metal fastening unit that grasps the mini bottle of hand sanitizer from two points, and secures it to the key housing. The size of the arms that bridge the gap between the keys and the edge of the keyboard can be standardized for maximum compatibility across brands and sizes. The key housing is attached to the clip fastening feature by way of the spring mechanism, which allows for the depressing mechanism to have autonomy of motion and the capacity to apply lateral pressure to the dispenser nozzle. The user would operate this embodiment by exerting downward pressure on the key housing, thereby engaging the depressing mechanism that applies lateral force to operate the dispenser and release a spray of hand sanitizer in the opposite direction of the keyboard (depicted in FIG. 4). This embodiment can be removable from the User Technology to which it attaches.

As shown in FIG. 1, the first preferred keyboard hand sanitizer attachment is comprised of two metal support units 2 that have a spring mechanism that is affixed to the underside of a plastic housing structure 1 that maintains the same size and feel as the standard keyboard "Enter" key. One end of each metal support unit 2 is equipped with a fastening clip feature 3 that allows it to support a small bottle of hand sanitizer 5. At the opposite end of each fastening clip are support and suspension arms 2 that are inserted into the face of the keyboard, and allow the embodiment to attach to the lip of the keyboard and suspend above the surface on which it rests. The user would operate this embodiment by exerting downward force on the plastic housing, thereby engaging the spray mechanism and releasing hand sanitizer product in the opposite direction of the keyboard. This and other embodiments can be removable.

Figure 2:
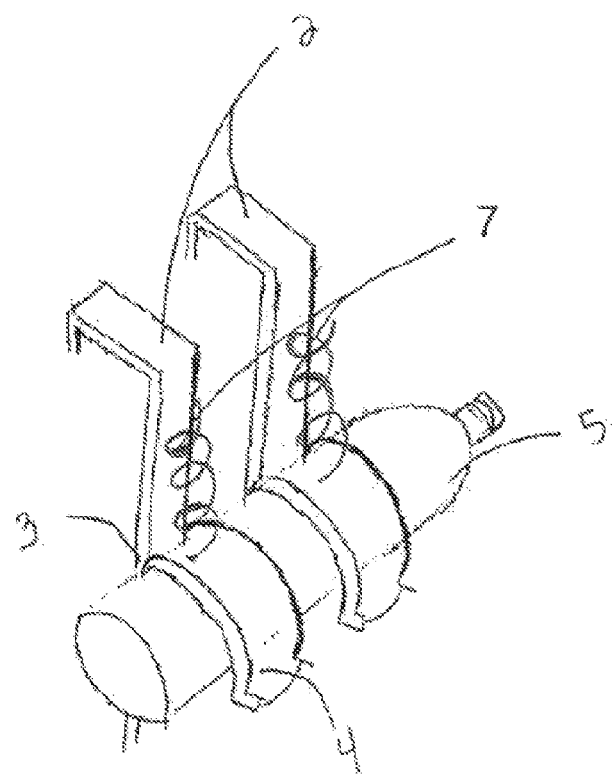
FIG. 2 is a perspective view of the support structures of a keyboard hand sanitizer attachment that support and suspend a small bottle of hand sanitizer from a keyboard or other electronic input device.

As shown in FIG. 2, both the fastening clip features 3 and the support and suspension arms 2 are an extension of two identical metal support systems. In this embodiment the suspension arms would be standardized for maximum compatibility across brands and sizes, and placed over the tip of the keyboard 6. These arms allow the fastening clip features 3 to suspend above the surface on which the keyboard rests, while the spring mechanism 7 attaches to the underside of the plastic housing.

Figure 3:
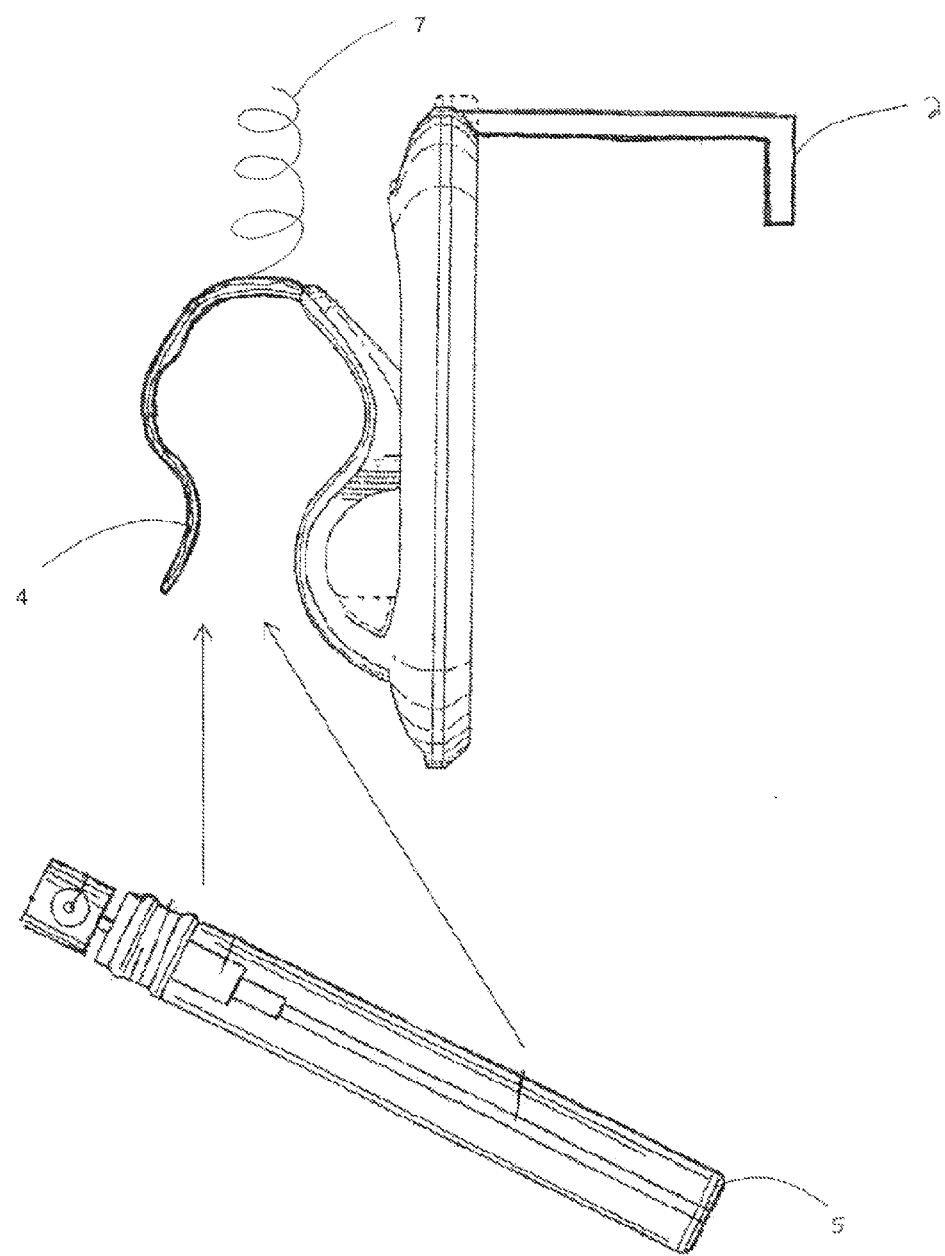
FIG. 3 is a drawing depicting an end view of the support structures of a keyboard hand sanitizer fastening clip system that displays the method by which a hand sanitizer or other Dispensable bottle is held therein.

As illustrated in FIG. 3, the attachment clips 4 of the support systems 2 can grasp the miniature bottle of hand sanitizer without a complicated fastening system. This allows a sanitizer dispensing bottle 5 to be removable and replaceable. Other fastening mechanisms may also be used in other embodiments of the invention. The spring mechanism 7 that rests atop the clip fastening feature 3 is connected to the underside of the plastic key housing, and serves as a conduit that allows the operator's downward force to engage the dispenser.

Figure 4:
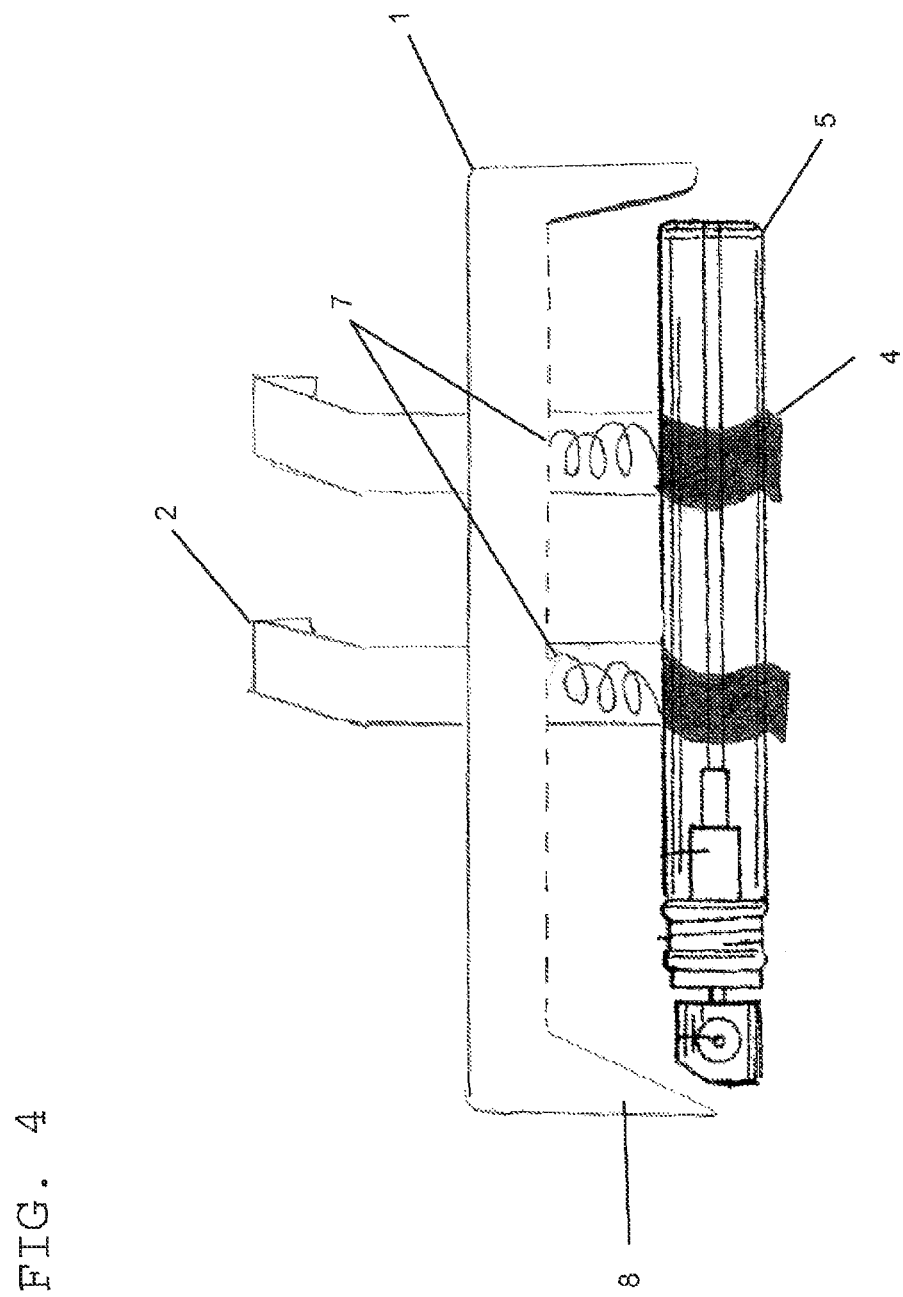
FIG. 4 is a drawing depicting a cross-sectional view of the enter key housing and the mechanism that depresses the nozzle of the hand sanitizer bottle, thereby releasing one or more Dispensable products.

As depicted in FIG. 4, the plastic "Enter" key housing 1 is affixed to the clip fastening feature 3 by way of the spring mechanism 7. Both the key housing K and the clip fastening feature 3 are suspended, and protrude outward from keyboard 6 and support systems 2, thereby enabling the user to engage the dispenser without removing the embodiment from its point of suspension. The attachment clips 4 affix the dispenser bottle to the clip fastening feature, and when a user exerts downward force on the plastic housing 1, the spring mechanism 7 engages the depressing mechanism 8, which applies lateral pressure to the dispenser nozzle and causes the product to be dispensed.

The foregoing describes the current preferred embodiment of the invention. Variations and modifications will be apparent to persons skilled in the art, without departing from the inventive concepts disclosed herein. For example, embodiments of the invention may attach directly or in proximity to various types of User Technology, such as desktop and laptop computers, iPads and other handheld devices, smartphones and "personal digital assistants", and other devices and technology, or components or accessories associated therewith. Additionally, and without limiting the foregoing, embodiments of the invention may store and/or dispense various types of Dispensables, such as hand sanitizers, soaps, detergents, cleansers and other hygiene products, tissues, wipes, alcohol rubs and similar products, cosmetics and other beauty products, and other dispensable or storable products related to hygiene, cleanliness and/or personal wellbeing, and embodiments may store one Dispensable or multiple Dispensables. Certain embodiments may be removable from the User Technology to which they attach and other embodiments may be permanently attached to such User Technology, as applicable.

All such modifications and variations are intended to be within the scope of the invention, as defined in the following claims.

The invention claimed is:

1. A device for dispensing one or more Dispensables in direct physical connection to the keyboard of User Technology, said device comprising:
   a housing structure;
   an attachment structure for attaching said device to said User Technology, wherein said attachment structure comprises an attachment mechanism for attaching said device to the keyboard of said User Technology and positioning said housing structure adjacent to and attached to the keyboard of said User Technology;
   a storage container for storing said one or more Dispensables; and
   a mechanical dispenser mechanism for dispensing said one or more Dispensables;
   wherein said housing structure further comprises an upper face above said storage container and mechanical dispenser mechanism and a lower support below said storage container and mechanical dispenser mechanism.

2. The device of claim 1, wherein said mechanical dispenser mechanism comprises a spring compressible by a user by exerting force on said spring, said spring attached at one end to said upper face and at the other end to said mechanical dispenser mechanism, said compression being communicated to said mechanical dispenser mechanism to dispense said one or more Dispensables in response to said compression.

3. The device of claim 1, wherein said User Technology is a desktop computer.

4. The device of claim 1, wherein said User Technology is a laptop computer.

5. The device of claim 1, wherein said device is detachable from said item of User Technology and reattachable to said or another item of User Technology.

6. The device of claim 1, wherein said housing structure is the size and shape of an "Enter" key.

7. The device of claim 1, wherein said attachment structure comprises a clip mechanism, which clip mechanism is configured to clip onto said keyboard.

8. The device of claim 7, wherein said clip mechanism is detachable from said User Technology.

\* \* \* \* \*